(12) United States Patent
Virtanen et al.

(10) Patent No.: US 8,718,740 B2
(45) Date of Patent: May 6, 2014

(54) BIOMEDICAL SENSOR

(75) Inventors: Juha Petri Virtanen, Helsinki (FI); Antti Kustaa Antipas Ylostalo, Helsinki (FI)

(73) Assignee: General Electric Company, Schenectady, NY (US)

( * ) Notice: Subject to any disclaimer, the term of this patent is extended or adjusted under 35 U.S.C. 154(b) by 184 days.

(21) Appl. No.: 13/327,799

(22) Filed: Dec. 16, 2011

(65) Prior Publication Data
US 2012/0157807 A1 Jun. 21, 2012

(30) Foreign Application Priority Data
Dec. 20, 2010 (EP) .................................. 10195887

(51) Int. Cl.
*A61B 5/0408* (2006.01)
*A61B 5/0424* (2006.01)
*A61B 5/0478* (2006.01)

(52) U.S. Cl.
USPC ........................... 600/372; 600/383; 600/391

(58) Field of Classification Search
CPC ............. A61B 5/0408; A61B 5/04087; A61B 5/0478; A61B 5/0424; A61B 5/6843; A61B 5/7221
USPC .......................................... 600/372, 383, 391
See application file for complete search history.

(56) References Cited

U.S. PATENT DOCUMENTS

2002/0188053 A1 12/2002 Zang et al.
2005/0137542 A1 6/2005 Underhill et al.

FOREIGN PATENT DOCUMENTS

WO 2006097085 A2 9/2006

OTHER PUBLICATIONS

European Search Report issued Jun. 16, 2011, pp. 1-5.

*Primary Examiner* — Lee S Cohen
(74) *Attorney, Agent, or Firm* — Global Patent Operation; Marc A. Vivenzio

(57) ABSTRACT

A biomedical sensor is provided. The biomedical sensor comprises a printed bio-potential electrode on the biomedical sheet sensor configured to provide an electrical contact with a surface to be measured, and a bi-stable printed electronic ink indicator provided on the biomedical sheet sensor and configured to indicate a loose contact of a bio-potential electrode operation by switching the color of the bi-stable indicator from a first color to a second color when a loose contact is detected.

13 Claims, 4 Drawing Sheets

BIOMEDICAL SENSOR

BACKGROUND OF THE INVENTION

1. Field of the Invention

Embodiments of the present invention relate generally to electrodes for obtaining biosignals from a recording surface, for example a skin of a subject.

2. Description of the Prior Art

When monitoring the vital signs or other physiological parameters of hospitalized patients, sensors are attached on patients' skin or catheters are inserted either into natural openings of the body or catheters are pierced through the skin. The common practice is to connect these sensors with electrically or optically conductive cables to measurement instruments. The instrument may reside either on bedside (e.g. multi-parameter patient monitors in an operating room (OR) or in an intensive care unit (ICU)) or it may be a relatively small box carried by the patient (e.g. ECG telemetry).

Infection control has become a big issue in a hospital environment. The term "disposable" as used herein refers to a single-use sensor which is used once and then disposed. Totally disposable sensors would make infection control easier. They would also streamline the care process by eliminating the need for cleaning the sensors. The use of disposable single-patient-use sensors prevents the spreading of infections and cross contamination inside the hospital. This also improves the care process by saving time and money. There are several disposable sensors available on the market such as a depth-of-anesthesia sensor, SpO2, ECG sensors, etc.

In patient-monitoring devices it is also important to ensure that the sensors are properly attached to the patient and that they provide sufficient signal quality so that the alarms and calculated parameters generated based on the signal are reliable. For this purpose, practically all patient monitors may analyze the signal quality continuously. They may also measure the electrical or optical properties of the sensor contact continuously or intermittently. In the case of insufficient contact or signal quality, the monitor prompts the user to check the particular sensor. The common way to indicate which sensor to check is to refer to it using an established naming system, such as the '10-20 electrode system' in EEG. The message on the monitor screen would be something like 'Poor ECG electrode contact, check electrode V5' or 'Poor EEG electrode contact, check electrode P3'. The electrode naming system is usually printed on the cover of a connector box, in which the individual electrode lead wires are combined into a single multi-wire cable. Obviously, this method of indicating the suspected electrode is complex and difficult to use, especially if the user is not familiar with the naming convention or if the electrodes are at non-standard locations.

Recent technological development has made it possible to build battery-operated sensors, which include means for performing the actual measurement, converting the measured signals into digital format, and transmitting wirelessly the measurement data and/or calculated parameters to a host device. Instead of transmitting the data in real time, it is also possible to store the data in local memory and download the data afterwards. These devices are referred to as wireless sensors. Wireless sensors provide obvious benefits for both caregivers and patients. The so-called 'cable clutter' has been recognized as one of the biggest issues in the care process of high-acuity patients. There are a lot of cables in the hospitals that also create issues with infections and the usability. By using wireless sensors one can reduce the amount of cables used in a hospital and improve the usability of the different parameters and the total care process. It is not necessary to remove all the cables, but a significant improvement would be achieved by removing a moderate number of leads or wires. This is because the tendency to tangle increases disproportionally with the number of cables. The patients that would benefit most from the wireless sensors are low-acuity patients. Being not physically tied to the patient monitor with lead wires, they are free to move around, for example, visiting the bathroom without assistance. Also in case of a small patient monitor carried by the patient, wireless sensors offer better reliability and are more comfortable for the patient.

However, in case of wireless, single-use sensors, the problem relating to identifying electrodes is even greater than in established ECG or EEG systems. Firstly, the sensors are often attached in non-standard locations, which makes the naming difficult, especially because there may not be an obvious place to print the electrode placement chart. And secondly, there may be no conventional bedside monitor with a display to indicate the location of the electrode with poor contact.

BRIEF SUMMARY OF THE INVENTION

According to an embodiment of the present invention, a biomedical sensor is disclosed. The biomedical sensor comprises a printed bio-potential electrode on the biomedical sheet sensor configured to provide an electrical contact with a surface to be measured, and a bi-stable printed electronic ink indicator provided on the biomedical sheet sensor and configured to indicate a loose contact of a bio-potential electrode operation by switching the color of the bi-stable indicator from a first color to a second color when a loose contact is detected.

BRIEF DESCRIPTION OF THE SEVERAL VIEWS OF THE DRAWINGS

Exemplary embodiments will be described in greater detail with reference to the attached drawings, in which.

DETAILED DESCRIPTION OF THE INVENTION

Figure 1:
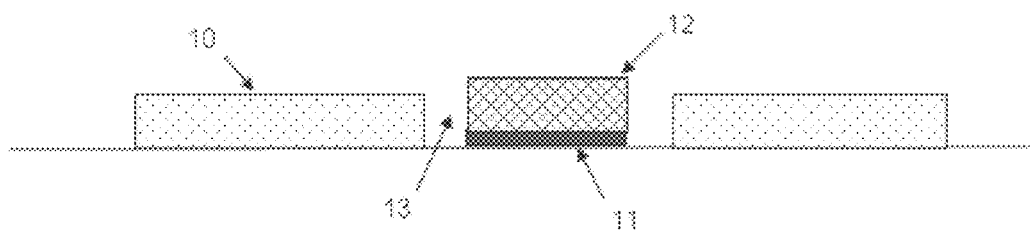
FIG. 1 illustrates an example of a prior art biomedical sensor.

Electrodes for measuring biosignals from a recording surface, for example the skin of a patient, may be generally classified as dry electrodes or wet electrodes depending on the presence of an electrolyte on the surface attached to the skin. Dry electrodes are mainly applied to the skin using an elastic band. An example of a dry electrode is a heart rate meter belt used in sports medicine. On the other hand, an electrode may be classified as a wet electrode in the presence of an electrolyte on the contact surface attached to the skin. A wet electrode may be attached to the skin using a conductive liquid, hydrogel or solid gel, e.g. electrolyte gel, to improve the electrical conductivity between the recording surface and the electrode sensing element, such as a silver/silver chloride (Ag/AgCl) electrode layer. Typical components of a conductive gel may include water (which acts as the solvent), water-soluble monomers which crosslink to give structure to the gel and which may also provide skin adhesion, humectant materials which reduce the dryout characteristics of the conductive gel, and electrolytes or salts, such as sodium chloride (NaCl) or potassium chloride (KCl) dissolved in water, which provide the ionic conductivity. A gel with a high salt content produces a better conductor than that obtained when using a gel with low salt content. One advantage of conductive gels over other conductive electrolytes is that they can be removed cleanly from the skin without leaving a residue. In addition, the use of a high salt content typically requires less skin abrasion at the time of application to reduce the impedance of the skin-electrode interface after subsequent electrode application. Consequently, biosignal measurement sensor electrodes with high salt content traditionally may have a limited shelf life (maximum storage time prior to use), for example, due to drying of the gel in the electrodes, and also due to the changes that may take place in the sensor materials. Wet gel electrodes provide better contact that dry electrodes: the contact impedance is lower and the signal bandwidth extends to lower frequencies. This is why dry electrodes are typically used in limited applications, such as heart rate measurement, whereas wet gel electrodes are used in diagnostic ECG, where various features of the signal are analyzed.

It should be appreciated that embodiments of the invention are not intended to be restricted to any specific sensor type but are applicable to any type of biomedical dry or wet sensor. Exemplary embodiments below are described in connection with biomedical sensors illustrated above are merely examples of sensors that use a conductive liquid, hydrogel or solid gel, commonly referred to as a conductive electrolyte or gel herein, to improve the electrical conductivity. Such electrolyte, such as conductive gel, must be protected from drying and creates a harmful high-humidity environment. GE Healthcare's a depth-of-anesthesia sensor is a good example of a printed sheet sensor. It contains a substrate, conductive traces, conductive barrier layer and dielectric layer printed with screen-printing, flexoprinting or any other equivalent process. It also contains electrolyte gel to enable biosignal measurement from living tissue. There are also various other sensors manufactured with similar technologies on the market.

Figure 2:
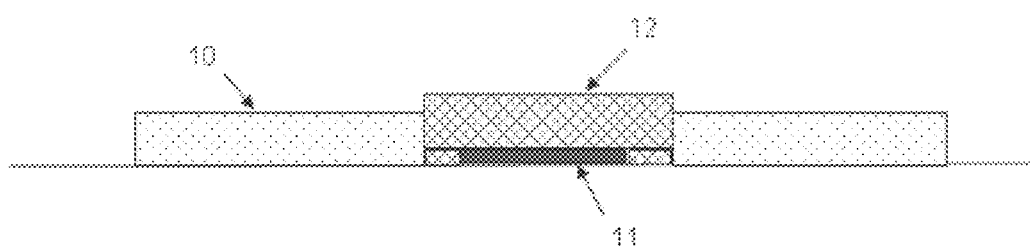
FIG. 2 illustrates another example of a prior art biomedical sensor.

FIG. 1 illustrates, in a side view, an example of a prior art biomedical sensor. Printing processes are particularly well suited for manufacturing single-use biomedical sensors. The standard materials used in such sensors are silver conductors and Ag/AgCl contact. Also carbon may be used as a conductor. All these materials are available as printing pastes. At the moment, the use of printing technology has just established its positions in manufacturing of passive ECG and EEG sensor sets. The exemplary sensor may include a planar substrate (e.g. a film of non-conducting material, such as plastic), a conductive electrode layer 11 (e.g. silver (Ag) that is chloridised chemically with gel, silver/silver chloride (Ag/AgCl), copper (Cu), carbon (C)), a gel-carrying element 12 (such as a sponge soaked with a conductive gel) overlaying the conductive electrode layer 11, and an adhesive layer 10 (e.g. an adhesive foam material) surrounding the gel-carrying element 12 (in the same planar plane) for attaching the electrode to living tissue, for example human forehead or chest. The surrounding adhesive layer 10 may be spaced apart from the gel-carrying element 12 such that a space 13 is provided between the surrounding adhesive layer 10 and the gel-carrying element 12. FIG. 2 illustrates, in a side view, another example of a biomedical sensor. The exemplary electrode may include a planar substrate (e.g. a film of non-conducting material, such as plastic), a conductive electrode layer 11 (e.g. silver (Ag), silver/silver chloride (Ag/AgCl), copper (Cu)), a conductive gel 12 in a solid form ("a solid gel") overlaying the conductive electrode layer 11, and an adhesive layer 10 (e.g. an adhesive foam layer) surrounding the solid gel 12 (in the same planar plane) for attaching the electrode to living tissue, for example human forehead or chest. In both examples, the conductive electrode layer 11 may contact the gel element 12 on one side (top side in FIGS. 1 and 2), and conducting traces (e.g. strips of conductive material provided on the substrate (not shown)) on the other side (bottom side in FIGS. 1 and 2). The electrode layer 11 is the interface at which ionic conduction through the conductive gel changes to electronic conduction to a monitoring/recording device. The traces, which may be printed or etched, for example, provide electrical connection between the electrode and an associated electronic circuit in the biomedical sensor patch, or via cables to the nearby monitoring device. The traces may also be printed Ag, or Cu, for example. In a typical high-performance electrode, a AgCl layer is chemically formed on top of a Ag conductor, or a Ag/AgCl layer is printed on a conductor made of Ag, Cu or C, for example. There may be a single electrode or electrode arrays containing multiple electrodes on the same substrate.

As noted above, all patient monitors may measure the signal quality or the electrical or optical properties of a sensor contact continuously or intermittently. In case of insufficient contact or signal quality, the monitor may prompt the user to check the particular sensor by means of displaying an appropriate alarm message on the monitor screen. The suspected electrode may be indicated using an established naming system. Obviously, this method of indicating the suspected electrode is complex and difficult to use, especially if the user is not familiar with the naming convention or if the electrodes are at non-standard locations. Thus, there is a need for improving a loose electrode indication, referred to as lead-off indication, herein.

The inventors considered an indicator system in which there is a light-emitting element close to each electrode (ideally on the top of the electrode) so that the monitor system drives the indicator through an electrode cable, but this approach would add complexity and cost in the system in the form of additional signal wires in the electrode cables and additional contacts in the electrode cable connector. Secondly, in case of a wireless sensor, a power source (typically a battery) in a wireless sensor is a scarce resource. Hence, constraints in power budget limit the usefulness of light-emitting indicators. The excessive load from light-emitting indicators is not acceptable. The issue with power consumption is emphasized, if one wants to build a bipolar indicator, e.g. a green light indicating a good contact and a red light indicating a poor contact. Thirdly, single-use wireless sensors are extremely cost-sensitive, so that the material and manufacturing cost related to any additional semiconductor component may be unacceptable.

According to an embodiment of the invention, a bi-stable indicator made of an electrochromic ink may be provided as a part of a biomedical sensor to indicate a loose contact of a bio-potential electrode operation by switching the color of the electrochromic ink indicator from a first color to a second color when a loose contact is detected.

As used herein, the concept called 'the color of the indicator' may generally refer to any observed hue, saturation or lightness changes of the indicator. This can be obtained in several physical means, which may include 1) a base layer of color A covered with a layer which cycles from clear to opaque color B, or 2) a layer whose spectral reflectance and/or absorption properties change from color A to color B, or 3) a layer, whose reflectance/absorption properties change with no change in spectral distribution.

In an exemplary embodiment of the invention, a substrate sheet, the biomedical sensor may be a disposable printed sheet sensor having a printed bio-potential electrode on a substrate sheet for providing an electrical contact with a surface to be measured.

Electrochromism is a phenomenon displayed by some materials of reversibly changing color when a burst of electric charge is applied. Various types of materials and structures can be used to construct electrochromic devices, depending on the specific applications. The color change is persistent and energy needs only be applied to effect a change of the color. The best-known application of electrochromic materials is electronic paper, or e-paper. E-paper, or electronic ink display, is a display technology designed to mimic the appearance of ordinary ink on paper. Unlike a conventional flat panel display, which uses a backlight to illuminate its pixels, electronic paper reflects light like ordinary paper. It is capable of holding text and images indefinitely without drawing electricity, while allowing the image to be changed later. As used herein, the terms electrochromism and electrochromic are intended to also encompass electrophoresis and electrophoresic materials as alternative phenomena and materials for implementing a bi-stable indicator. Electrophoresis is the motion of charged particles suspended in a liquid in response to an electric field. Positively charged particles move toward the cathode, and negatively charged particles move toward the anode. If these particles are colored, the display shows different colors to the user as the particles move. Thus, electrophoresis may be used to switch pixels on and off and to change color of an indicator or display.

In exemplary embodiments of the invention, a bi-stable electrochromic indicator in a biomedical sensor consumes energy only when the color is changed, i.e. when a relatively small voltage is applied. Basically no electric power may be needed to maintain the color change. Hence, the power consumption is very small. Also the information of the indicator remains visible, even if a battery runs out. Thus, a bi-stable electrochromic indicator is ideal for a battery-operated, self-powered biomedical sensor.

In practice, the electrochromic materials may not be completely bi-stable, but there may be a certain decay time associated with the color change. This time may be of the order of approximately 10 minutes, for example. In exemplary embodiments, the color change of a bi-stable electrochromic indicator may be maintained by refreshing it with a voltage pulse at appropriate intervals, e.g. with a narrow low-power voltage pulse at regular intervals. Each electrochromic material has a particular state (color, tint) towards which it decays. In exemplary embodiments of the invention, a basic state (color) towards which the employed electrochromic material decays may be selected to indicate a loose/poor contact so that the user is alarmed, even if the battery runs out or the refreshment fails.

In embodiments of the invention, a biomedical sensor may further be provided with a further electrochromic indicator indicating a battery charge level. The battery charge level indicator may be a simple bi-stable electrochromic indicator wherein a first color may indicate a sufficient battery level, and a second color may indicate a low battery or a low power situation. A color change may be caused by applying a relatively small voltage. Alternatively, a battery charge level indicator may be a multi-level indicator, such as a bar graph. For example, there may be two or more bi-stable electrochromic indicators, each corresponding to and indicating a specific battery charge level. A first color may indicate a sufficient battery level, and a second color may indicate a low battery or a low power situation. Also in case of the battery charge level indicator, the color change of the bi-stable electrochromic battery-level indicator(s) may be maintained by a refreshing voltage pulse at appropriate intervals. In exemplary embodiments of the invention, a basic state (color) towards which the employed electrochromic material decays may be selected to indicate a low battery level.

In embodiments of the invention, a biomedical sensor may further be provided with a further electrochromic indicator indicating a remaining or exceeded use time or storage time. The battery charge level indicator may be a simple bi-stable electrochromic indicator wherein a first color may indicate that there is still use/storage time remaining or that the use/storage time is not exceeded, and a second color may indicate that a use/storage time is exceeded. A color change may be caused by applying a relatively small voltage. Alternatively, a time indicator may be a multi-level indicator, such as a bar graph. For example, there may be two or more bi-stable electrochromic indicators, each corresponding to and representing a specific remaining use/storage time.

According to an embodiment of the invention, the electrochromic indicator(s) may be manufactured in the same printing process with the remaining components of the sensor. Common printing techniques can be employed, such as silk screen printing, flexography, roll-to-roll, etc. Electrochromic inks, which are suitable for printing indicators on bio-potential electrodes, are commercially available. Examples of ink manufacturers include Chameleon Optics Inc., E Ink Corporation, and NTERA, Inc.

According to an embodiment of the invention, a sensor may have a hybrid structure, where the electrochromic indicator(s) may be manufactured separately, and attached on the sensor, e.g. by adhesive.

In embodiments of the invention, a detector circuit may be provided in the biomedical sensor and configured to detect a loose contact of the electrode to the measuring surface, such as a human's skin, during operation, and to switch the color of the bi-stable electrochromic indicator from the first color to the second color when a loose contact is detected.

In embodiments of the invention, at least one battery may be provided in the biomedical sensor to provide an electrical power to the bi-stable electrochromic indicator, and to associated electronic circuits, such as a lead-off detector. Any type of battery may be used. However, if a changeable or rechargeable battery is used, it will require charging or special handling of the batteries. A changeable or rechargeable battery may also require special installation when starting to use the sensor because the battery may need to be added to the sensor separately. Difficult maintenance and high cost related to batteries has been the key factor in preventing wireless sensors from becoming widely accepted. Moreover, the batteries typically used need to be recycled. The battery replacement cycle should match the hospital's daily routine and the disposed batteries and sensors should require no special handling.

According to an exemplary embodiment of the invention, the at least one battery comprises a disposable printed battery on a disposable sensor for energizing the bi-stable electrochromic indicator. Soft batteries, such as printed batteries are manufactured using methods to make them disposable. These batteries do not contain any environmentally hazardous materials and can be disposed with the sensors without any special handling, such as circulation of batteries. A disposable power source (with capacity for operation over a required monitoring period, such as 24 hours) on a biomedical sensor is a perfect fit with hospital's logistics and care process. Infection control in hospitals is improved. No extra work from maintaining or special handling of the batteries of biomedical sensors is needed.

According to exemplary embodiments of the invention, the at least one disposable printed battery is arranged in a hermetically sealed compartment on the substrate sheet. Wet sensors with an electrolyte on the contact surface may be stored within an enclosure or a package, which provides a proper atmosphere to prevent the drying of the electrolyte and prolong the shelf life of the sensors. Because of the humidity (up to 99%), and the existence of the salt from the electrolyte, the sealed humidity-impermeable enclosure or package may create an atmosphere, which is harmful for several materials. This atmosphere corrodes many materials and chlorides them and it requires special attention to the material selections of the sensor. Disposable printed batteries should not contain any hazardous materials and can be disposed with the sensors. This creates limitations on the material selections. Materials of the printed batteries cannot be changed to withstand the high humidity and corroding atmosphere. A typical packaging solution for the soft batteries is to use plastic or paper based electrically non-conductive material in making the package. Using of paper-based package is not an option in the high humidity environment because the humidity and the salt would then absorb to the paper and short circuit the battery terminals. Some printed batteries may include wet electrolytes and they may be sealed within a plastic sheathing film to prevent liquid evaporation, and are therefore closed electrochemical cells. Being closed cells, these batteries may tend to swell upon storage due to undesirable gas formed within the battery.

Embodiments of the invention provide a disposable wet, self-powered biomedical sensor comprising a conductive electrolyte material, capable of withstanding a high humidity and saline storage environment, while allowing use of environmentally non-hazardous materials in a battery such that no special handling is required at disposal of the sensor. A disposable battery is provided in a hermetically sealed compartment on the sensor structure, such that the unified battery-electrode combination can be stored within the same package or enclosure, such as within the same pouch, having an internal atmosphere with high humidity level, even up to about 99% and saline content since pouch contains electrolyte gel. As a result, a disposable wet, self-powered biomedical sensor is provided that offers a long shelf life, e.g. a shelf life of the order of 6-12 months or more.

According to an embodiment of the invention, the battery may be manufactured in the same printing process with the remaining components of the sensor, or where the battery may be manufactured separately, attached on top of a sensor substrate sheet, e.g. by adhesive, and covered by printing or laminating or other relevant process with humidity and salt resistant layer to enable adequate shelf life. Common printing techniques can be employed, such as silk screen printing, flexography, roll-to-roll, etc. The battery may be covered with humidity and salt resistant layer by printing or laminating or other relevant process. Alternatively, the battery may be manufactured separately and encapsulated hermetically with a humidity resistant material prior to attaching it on top of a sensor substrate sheet, e.g. by adhesive. A substrate may be used that is tolerant to humidity and optimized for conductive ink printing. Substrate manufacturers may use chemical treatments for the substrate to assist adhesion to water or solvent based printing and coating systems. This also creates a homogenous printing surface that is humidity tolerant. One example of a possible substrate is double-sided chemically coated polyethylene terephthalate (PET) film. In an exemplary embodiment of the invention, there is a humidity resistant layer, such as dielectric layer or a metal layer, manufactured between the substrate and the battery. In another exemplary embodiment, the humidity resistance is provided by the substrate itself, or by any other intermediate layer, and the further special-purpose humidity resistant layer between the substrate and the battery can be omitted. In exemplary embodiments of the invention, the battery manufactured or provided on the substrate may be covered from the top side (the side away from the substrate) with a humidity and heat resistant dielectric layer. There are several dielectric inks available, which are designed for humid conditions. One example of this type of dielectric ink is a UV curing dielectric. Similar material may be used to provide a "humidity resistant layer" between the substrate and the battery. Alternatively, a metal layer (such as aluminum) may be used to make the battery humidity and salt resistant. The metal layer may be provided by printing or laminating, for example. As a further alternative, instead of a dielectric or metal layer, another humidity resistant material may be used to protect the battery layer, such as glass.

Figure 3:
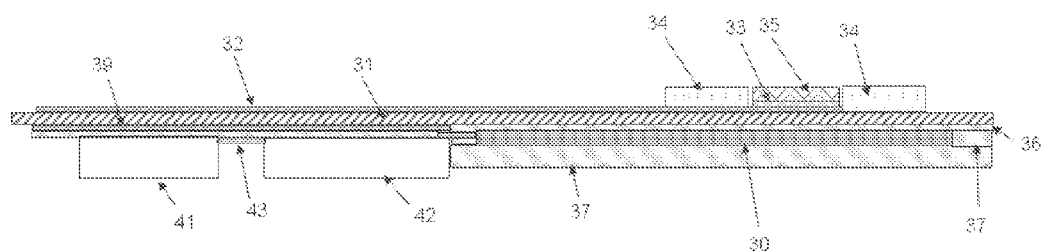
FIG. 3 is a cross-sectional side view of a biomedical sensor according to an embodiment of the present invention.

An illustrating example structure of a biomedical wet, self-powered sensor, which comprises a conductive electrolyte material and withstands a high humidity and saline storage environment, is shown in FIG. 3. The exemplary sensor is manufactured on a planar substrate 31 by a printing process, laminating process, or any other process which is suitable for creating material layers, or by a combination of two or more processes. For example, some of the layers may be manufactured by printing and other layers by laminating. The substrate 31 may be made of any suitable substrate material, such as those discussed above with reference to FIGS. 1 and 2.

Figure 5:
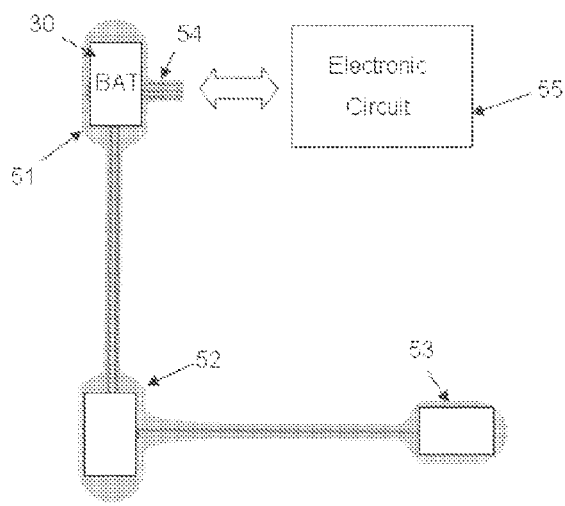
FIG. 5 is a top view of a biomedical sensor according to an embodiment of the present invention.

In the example structure shown in FIG. 3, components of a conventional type of biomedical wet sensor may be provided on a first, flat, surface of the substrate 31. More specifically, a conductive electrode layer 33 (e.g. silver (Ag), silver chloride (AgCl) on top of silver t(Ag) trace, silver/silver chloride (Ag/AgCl), copper (Cu)), a gel element 35 (such as a sponge soaked with a conductive gel) overlaying the conductive electrode 33, and an adhesive member layer 34 (e.g. an adhesive foam material) surrounding the gel element 35 (in the same planar plane) for attaching the electrode to living tissue, for example human forehead or chest, may be manufactured on the first surface of the substrate 31. For example, in the case the conductive electrode 33 and the gel element 35 have a circular shape in a plane parallel to the first surface of the substrate 31, the surrounding adhesive member may be ring-shaped such that the inner diameter of the adhesive member is large enough to accommodate the electrode 33 and the gel element 35. The conductive electrode layer 35 may contact the gel element 35 on one side (top side in FIG. 3), and conducting traces 32 (e.g. strips of conductive material) provided on the substrate 31 on the other side. The traces 32 provide electrical connection between the electrode 33 and an associated electronic circuit (such as an electronic circuit 41) in the biomedical sensor patch, or via cables to the nearby monitoring device. The traces may be made of Ag or Cu, for example. Although a single electrode is shown in this example, there may be multiple electrodes on the same substrate. An example of a biomedical sensor having multiple electrodes is shown in FIG. 5. It should be appreciated that embodiments of the invention are not intended to be restricted to any specific electrode type but are applicable to any type of biomedical electrode. Thus, any kind of biomedical electrode configuration may be provided on the first surface of substrate 31 in place of the configuration shown in FIG. 3.

In the example shown in FIG. 3, a planar printed battery 30 is encapsulated by a humidity resistant material on the opposite second flat surface of the substrate 31. This configuration minimizes the substrate area required. However, it should be appreciated that the battery may be located on any surface and at any location on the substrate 31. The printed battery 30 may be sandwiched between humidity-proof material layers 36 and 37 on the substrate sheet 31. Although a special-purpose humidity resistant layer 36 located between the substrate 31 and the battery 30, the humidity resistance may be provided by the substrate itself, e.g. by treatment or coating its surface, in which case the special-purpose humidity resistant layer 36 may be unnecessary and may be omitted. There may also be one or more intermediate layers between the humidity resistant layer 36 and the substrate 31.

Figure 4:
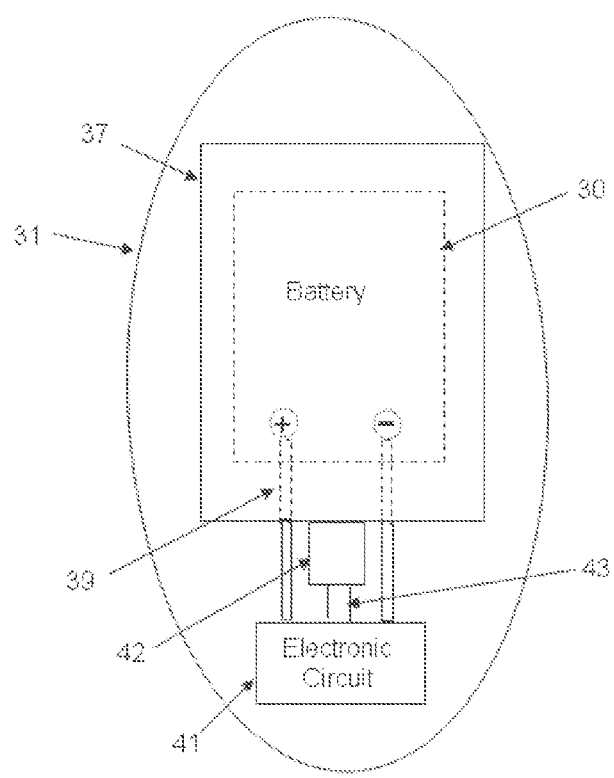
FIG. 4 is a top view of a biomedical sensor according to an embodiment of the present invention.

The battery 30 may be printed or otherwise attached on the humidity resistant layer 36. For example, the battery 30 may be separately manufactured, e.g. commercially available battery, which is attached in a suitable manner, such as with adhesive. The battery 30 may be covered from the top side (the side away from the substrate 31) with the second humidity resistant layer 37, for example by printing or laminating. The humidity resistant layer 37 may be a dielectric layer or metallic layer, for example. The metallic layer may be an aluminum layer or film, for example. The humidity resistant layer 37 may be made of the same or different material as that of the humidity resistant layer 36. In the exemplary embodiment, the top humidity resistant layer 37 and the humidity resistant layer 36 below the battery may be manufactured to join at the surrounding area beyond the periphery of the battery so as to encapsulate the battery 30 into a hermetically sealed compartment (a dry cavity) protected from the surrounding humid and saline atmosphere. Alternatively, the top humidity resistant layer 37 and the humidity resistant layer 36 below the battery may be sealed together by means of a peripheral seal or layer manufactured at the periphery of the battery so as to encapsulate the battery into a hermetically sealed compartment protected from the surrounding humid and saline atmosphere. In the example structure, conductive traces or wires 39 are provided to extend through the humidity resistant encapsulation of the battery 30 so as to provide the supply voltage to an electronic circuit outside the encapsulation (such as an electronic circuit 41 as shown in FIG. 4). Conductive traces 39 may also be provided on the second surface of the substrate 31 to function as supply voltage buses.

Flexible "printable" batteries are available on the market. For example Enfucell Inc. makes flexible and thin batteries using low cost, environmentally friendly, materials. The main active components in the batteries are zinc, manganese dioxide and zinc chloride as an electrolyte. When disposed, these batteries require no special treatment, but can be thrown into a normal waste basket together with the electrode. The batteries are manufactured by printing in a roll-to-roll process. SoftBattery® from Enfucell Inc. is manufactured with Enfucell allPrinted™ technology. The same or similar technology may be used also when manufacturing the battery 30 on the substrate by printing in the same process with the remaining components of the sensor.

It should be appreciated that, instead of a disposable printed battery 30, any type of battery may be used, including a changeable or re-chargeable battery. However, such batteries will require charging or special handling of the batteries, as noted above. It is also possible that the power source is external to the sensor patch, being located at a monitoring device connected to the sensor patch.

In the example structure shown in FIG. 3, an electrochromic indicator element 42 may be provided on the sensor substrate. The control input, e.g. the voltage pulse for changing or refreshing the color, may be applied from the associated electronic circuit over conductive traces 43. The electrochromic indicator(s) 42 may be manufactured in the same printing process with the remaining components of the sensor. Common printing techniques can be employed, such as silk screen printing, flexography, roll-to-roll, etc. Electrochromic inks, which are suitable for printing indicators on bio-potential electrodes, are commercially available. Examples of ink manufactures include Chameleon Optics Inc., E Ink Corporation, and NTERA, Inc. Alternatively, a sensor may have a hybrid structure, where the electrochromic indicator(s) 42 may be manufactured separately and attached on the a sensor, e.g. by adhesive.

FIG. 4 is a top view of the exemplary biomedical sensor shown in FIG. 3. In the example shown in FIG. 4, the substrate 31 of the sensor is oval-shaped, but it may have any arbitrary shape depending on the application. The battery 30 may be covered by the top humidity resistant layer 37, which extends beyond the periphery of the battery 30, thereby encapsulating the battery 30. Conductive traces or wires 39 may extend from the (+) and (−) terminals of the battery 30 through the humidity resistant encapsulation 37 to the electronic circuit(s) 41 outside the encapsulation. Alternatively, the electronic circuit(s) 41 may be within the encapsulation, or remote from the battery. The electrochromic indicator element 42 is shown as located on the sensor substrate between the battery 30 and the electronic circuit 41. However, it should be appreciated that the electrochromic indicator element 42 may be located at any position on the sensor from which it can be seen by the user during the use.

In a still alternative exemplary embodiment, the battery 30 may be manufactured separately, the humidity resistant layers 36 and 37 may formed by a package, such as a pouch of humidity resistant material, within which the battery 30 may be inserted and sealed in order to hermetically encapsulate the battery 30, such that the package encapsulating the battery 30 can be attached on the substrate 31. The package may be a metallic (e.g. aluminum) pouch similar to a pouch that is used for packaging of biomedical wet electrodes. Suitable traces or wires may be taken out of the encapsulated battery to provide the supply voltage to an external electronic circuit (such as circuit 41 as shown in FIG. 4). The resulting hybrid structure may result in a similar arrangement as shown in FIGS. 3 and 4, the reference numerals 36 and 37 depicting the package or pouch of the battery 30.

FIG. 5 is a top view of another exemplary biomedical sensor having multiple electrode patches 51, 52, 53. One or more of the electrode patches may be provided with a printed battery 30 and/or an electrochromic indicator element 42. The electrode patch 51 may have a connector 54 for connecting a separate electronic circuit 55 to which biosignals and/or the supply voltage from the battery 30 are delivered. In an exemplary embodiment, the electronic circuit 54 may be reused, while the biomedical sensor with the battery or batteries 30 is a disposable single-use product.

Figure 6:
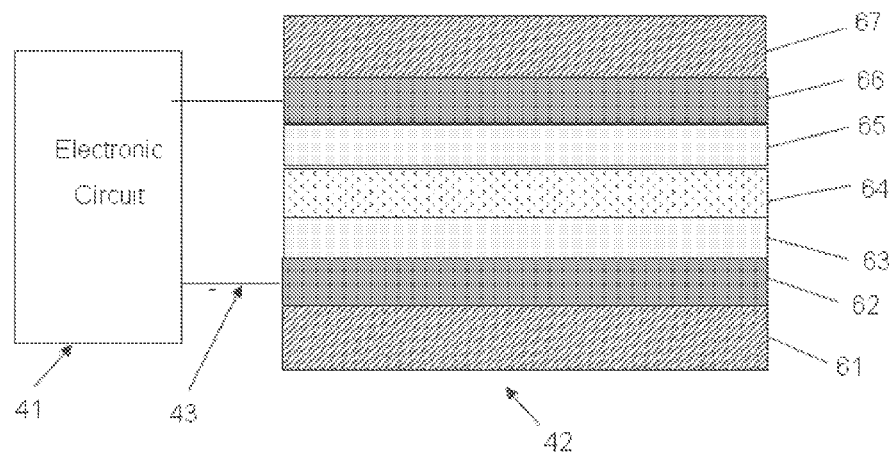
FIG. 6 is a side view of an electrochromatic indicator element according to an embodiment of the present invention.

An exemplary structure of the electrochromic indicator element 42 is shown in FIG. 6. The electrochromic element 42 may have a sandwich structure that may be printed on a biomedical sensor, or it may be manufactured separately and attached to the biomedical sensor. Typically, there may be two main types of electrochromic elements, the absorption/transmission (A/T) type and the reflective type. In the absorption/ transmission type, the active electrochromic material 63, 65 may be coated onto a transparent glass or plastic substrate 61, 67 and driven by a low voltage source, such as from 1.5 VDC to 5 VDC. The outer two layers on each side of the element make up a transparent conductive substrate or an electrode that comprises a transparent non-conductive plastic or plastic substrate 61 or 67, on which a transparent conductor 62 or 66, respectively, is applied. Suitable transparent conductive plastic substrates, such as indium-tin-oxide (ITO) on polyethylene terephthalate (PET) are commercially available. Sandwiched between the transparent conductors 62 and 66 are a positive electrochromic layer 65, an ion-conducting adhesive or an electrolyte (such as a viscous gel) 64, and a negative electrochromic layer 63. The electrochromic layers 63 and 65 are where the color changes occur. These layers can be continuous coatings, printed patterns, or individually addressed pixels. When a voltage is applied between the transparent conductors 62 and 66, e.g. via the traces 43 from the electronic circuit 41, cations (i.e. ions with a positive charge) are removed from the positive electrochromic layer 65 and injected into the negative electrochromic layer 63. As a result, both electrochromic layers 63 and 65 will change color from a first color to a second color, e.g. from a transmissive state (clear) to a colored state. When the polarity of the voltage applied between the transparent conductors 62 and 65 is reversed, cations are removed from the negative electrochromic layer 63 and injected into the positive electrochromic layer 65. Both electrochromic layers will change color from the second color to the first color, e.g. from a colored state to a transmissive state (clear). Hence, the electrochromic element 42 may switch between two states, colored and transmissive, or between two colors. The ion-conducting adhesive or electrolyte 64 allows the passage of cations, but prevents the passage of electrons so that the element 42 does not short circuit electrically. The tint of the electrochromic element 42 can be adjusted by setting the applied voltage. A reflective type of the electrochromic element 42 may have a similar structure to that presented in FIG. 6 with the exception that one electrode 61,62 or 66,67 is non-transmissive, e.g. made of Mylar foil coated by gold.

In exemplary embodiments shown in FIGS. 3 and 6, the biochromatic element 42 is driven from the electronic circuit 41. The electronic circuit 41 may be any circuit capable of providing the reversible voltage pulse to the biochromatic element 42. In a simple configuration the electronic circuit 41 may be a driver circuit controlled by a signal from a monitoring device or an external control device. As a slightly more complicated example, the electronic circuit 41 in the biomedical sensor may comprise a detector circuit configured to detect a loose contact of the electrode to the measuring surface, such as a human's skin, during operation and to switch the color of the bi-stable electrochromic indicator from the first color to the second color when a loose contact is detected.

In the following, three exemplary methods are described as candidates for a loose electrode, or lead-off detection.

In terms of power consumption, as well as cost and complexity of the electronics, so called 'DC lead-off' detection may be the most economical one. A DC current of the order of tens of nano-amperes may be fed through each electrode using a typically high-value resistor, such a resistor in range of 10 to 100 Mohm and a low-voltage, e.g. 2 to 5 V, DC excitation. If the electrode gets loose, the voltage of the input line rises up to the excitation voltage. Typically a separate DC-coupled amplifier or comparator may be used in parallel with the ECG preamplifier for detecting the increased DC-level. The DC leadoff detection may be most suitable for Ag/AgCl electrodes with large to moderate surface area. It may tend to polarize electrodes of any other material or needles with tiny surface area. Also, it may be difficult to control the detection threshold (in terms of contact impedance at about 20 Hz) precisely. DC leadoff detection also potentially reduces the effective input impedance of the amplifier to 10-100 Mohm level depending on the implementation.

AC leadoff detection using a frequency above the signal band, i.e. at about 500-30000 Hz, does not polarize the electrodes. Hence, it enables use of a larger variety of electrode materials and geometries on the cost of increased complexity of the electronics and potential compatibility issues with other biopotential measurements. Similarly, as with the DC lead-off method, the AC leadoff method is an indirect predictor of the contact impedance at EEG or ECG frequency band.

Intermittent impedance measurement at signal frequency band, e.g. 20 Hz is a true contact impedance measurement, rather than continuous leadoff check. It provides accurate measurement of the contact impedance on the cost of complicated electronics and need to interrupt the recording for the impedance measurement. Intermittent impedance measurement may typically be used with EEG in addition with DC leadoff detection.

Figure 7:
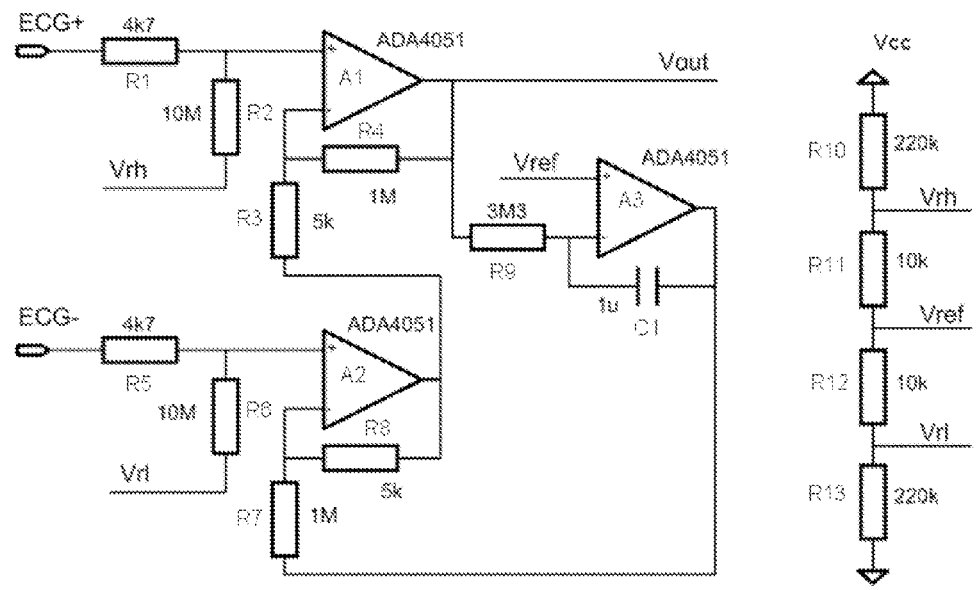
FIG. 7 is a circuit diagram of a preamplifier/detector according to an embodiment of the present invention.

FIG. 7 is a circuit diagram of an exemplary electrocardiograph (ECG) preamplifier designed so that it is possible to both amplify the ECG signal and detect the leadoff situation with a minimum number of components. There are no separate paths for ECG and leadoff signals, but a leadoff situation is detected as the ECG signal is pulled to the supply voltage. The design consists of a two-amplifier differential stage A1 and A2, in which high-pass filtering (A3, R9, C1) has been implemented in the feedback loop. The gain settings have been adjusted so that during normal operation, when the DC offset voltage between two electrodes is below a predetermined threshold level, the feedback amplifier A3 removes the DC component completely from the ECG signal. When the DC offset exceeds the predefined threshold, of the order of 50 mV, the output of the feedback amplifier saturates, which also drives the output of the differential amplifier into saturation. This state is identified as leadoff situation.

More specifically, the exemplary ECG preamplifier may comprise three amplifier components A1, A2 and A3 to measure one channel of ECG from only two electrodes. The ECG+ channel is connected via an input protection resistor R1 to a non-inverting input of the amplifier A1. Similarly, the ECG-channel is connected via an input protection resistor R5 to a non-inverting input of the amplifier A2. Instead of using a separate ground electrode, the both inputs of the operational amplifiers A1 and A2, and thereby each electrode, may be connected to an individual reference voltage Vrh and Vrl with a respective large resistor R2 and R6, e.g. 10 Mohm resistor. This arrangement ensures that the average potential of the patient is pulled to the mid-point between Vrh and Vrl.

Normally, a ground electrode has two different functions. It ties the internal ground potential of the preamplifier to the same potential with the patient, which function is now substituted with the function of resistors R2 and R6. Ground electrode also attenuates the common-mode voltage between the patient and the preamplifier at frequencies around mains voltage frequencies, i.e. 50 or 60 Hz. However, in small battery-operated devices, the electric fields from ambient tend to couple with similar mechanisms both to the sensor and to the patient's body. Hence, as a first approximation, no common mode voltages are generated between the amplifier and the patient. This enables the drop out of the separate ground electrode altogether.

Differential amplifier stages as described above can be connected so that they share a common electrode, making it is possible to measure two ECG channels from three electrodes, as in patches 51, 52 and 53 shown in FIG. 5.

The voltages Vrh, Vref, and Vrl may be derived from the supply voltage Vcc with a voltage divider network comprising resistors R10, R11, R12, and R13. Leadoff detection may be based on very small level (e.g. nanoampere level) DC currents through these resistors R2 and R6. If an electrode gets loose, the output of the respective differential amplifier A1 or A2 saturates. The resistors R2 and R6 may be tied to DC voltage sources of a few hundred millivolts. These voltages have been selected so that during normal operation the currents balance each other, and so that any single loose electrode can be identified based on the amplitude and/or polarity of the DC voltage.

The electronic circuit 41 or 55 may be any electronic circuit associated with the specific biosignal measurement. For example, the electronic circuit may comprise a signal amplifier, a signal processor, a data processor, a data memory, a wireless transmitter, a wireless transceiver, a wired or wireless communication interface, or any combination thereof. For example, the electronic circuit may comprise an ECG-amplifier with body area network connection and operated (e.g. over 24 hours) from the soft battery 30. When the electronic circuit is provided with a wireless transmitter, wireless transceiver, or a wireless communication interface, a self-powered wireless biomedical sensor is achieved. When the electronic circuit is provided with a memory, measured biosignal data may collected and stored in the memory energized by the battery 30 over a predefined period of time for subsequent downloading to a reading or monitoring device. The electronic circuit (e.g. an amplifier, memory and/or transmitter) may be either a separate piece of hardware (such as the electronic circuit 55 in FIG. 5), or the electronics may be built to be part of the disposable electrode sheet (such as the electronic circuit 41 in FIG. 4).

Figure 8:
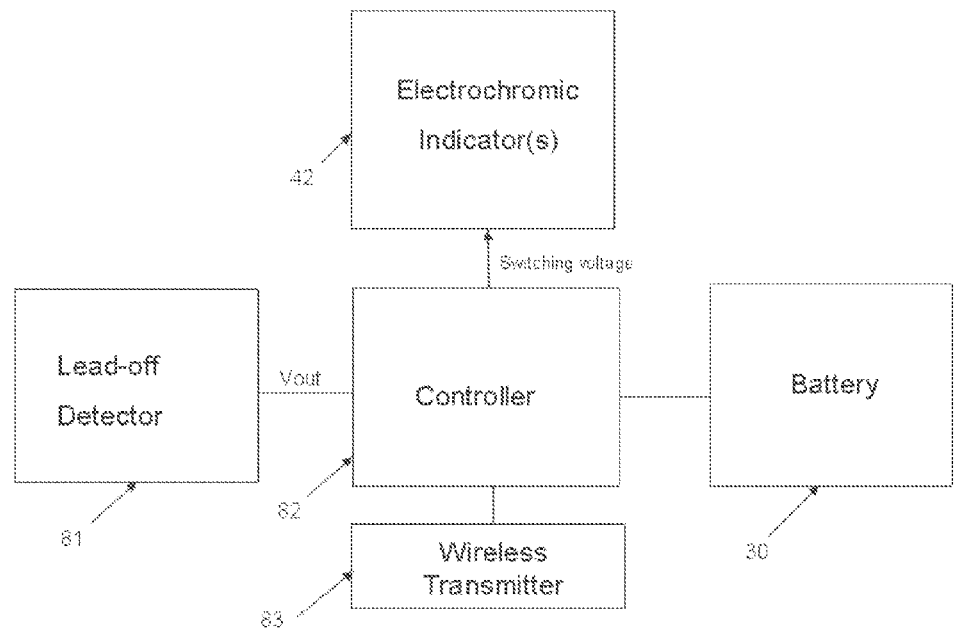
FIG. 8 is a block diagram of an exemplary electronic circuitry in a wireless biomedical sensor according to an embodiment of the present invention.

FIG. 8 is a block diagram illustrating exemplary electronic circuitry on a wireless sensor. Lead-off detector 81 may be an ECG preamplifier such as that shown in FIG. 7. Detector 81 provides a biosignal/lead-off signal to a controller 82. Controller 82 may be a microcontroller or a microprocessor, for example. The controller 82 may be connected to a wireless transmitter 83 for transmitting the measured biosignals. In case the output Vout from preamplifier/lead-off detector 81 indicates a loose electrode (e.g. the voltage Vout is pulled to the supply voltage Vcc), the controller 82 may supply a switching voltage (e.g. a voltage pulse) to a respective electrochromic indicator 42. All circuits may be powered from a battery 30. The controller 82 may also monitor the charge level of the battery to detect a low battery or an empty battery. The controller 82 may supply a switching voltage to one or more electrochromic indicator 42 to indicate the battery charge level or an empty battery.

Embodiments of the invention provide various advantages. The lead-off indicator may be located where it is really needed. Low power consumption is combined with clear visibility of the lead-off indicator. Low-cost manufacturing process can be used. A low cost, highly integrated solution is enabled. Additionally, there is a capability to indicate empty batteries. The local lead-off indicators are particularly well suited for a wireless sensor, in which there is no need to carry the indicator control signals over a connectors, which would increase the size and cost of the connector.

This written description uses examples to disclose the invention, including the best mode, and also to enable any skilled person to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A biomedical sensor, comprising:
   a printed bio-potential electrode on a substrate sheet configured to provide an electrical contact with a surface to be measured;
   a bi-stable printed electronic ink indicator switchable from a first color to a second color to indicate a loose contact of a bio-potential electrode operation; and
   a lead-off detector configured to detect a loose contact of the printed bio-potential electrode with the surface and to effect color switching of the bi-stable printed electronic ink indicator from the first color to the second color when a loose contact is detected.

2. The biomedical sensor according to claim 1, wherein the bi-stable printed electronic ink indicator comprises a bi-stable electrochromic indicator or a bi-stable electrophoretic indicator.

3. The biomedical sensor according to claim 1, wherein the bi-stable printed electronic ink indicator comprises an ink material having a predetermined decay time from the second color to the first color, and wherein a color change of the bi-stable printed electronic ink indicator is maintained by refreshing it with a voltage pulse at appropriate intervals.

4. The biomedical sensor according to claim 3, wherein the second color corresponds to a basic state towards which the ink material of the bi-stable printed electronic ink indicator decays.

5. The biomedical sensor according to claim 1, wherein the sensor has a hybrid structure.

6. The biomechanical sensor according to claim 5, wherein the lead-off detector is a direct current lead-off detector, an alternating current lead-off detector, or a contact impedance meter, and wherein the lead-off detector is configured to perform an intermittent impedance measurement at a signal frequency band.

7. The biomedical sensor according to claim 5, wherein the lead-off detector is a part of a biosignal preamplifier configured to both amplify the biosignal and detect a loose contact.

8. The biomedical sensor according to claim 7, wherein the biosignal preamplifier comprises:
   a differential amplifier stage comprising inputs connected to at least two electrodes, and an amplified biosignal output;
   at least two resistors at the inputs of the differential amplifier stage configured to feed respective at least two DC currents to respective at least two electrodes;
   a feedback amplifier loop with a high-pass filtering configured to remove a DC component from the amplified biosignal output and to feedback the amplified biosignal output;
   wherein the feedback amplifier loop is configured to saturate due to a loose contact of one of the at least two electrodes and to cause pulling of the amplified biosignal output up to approximately a supply voltage, wherein the pulled up amplified biosignal output indicates a loose electrode.

9. The biomedical sensor according to claim 1, further comprising at least one disposable printed battery.

10. The biomedical sensor according to claim 9, wherein the at least one disposable printed battery is arranged in a hermetically sealed compartment on the substrate sheet.

11. The biomedical sensor according to claim 1, further comprising at least one additional bi-stable printed electronic ink indicator configured to indicate a battery charge level, and an additional bi-stable printed electronic ink indicator configured to indicate a remaining or exceeded use time or storage time of the biomedical sensor.

12. The biomedical sensor according to claim 1, wherein the biomedical sensor is a wireless biomedical sensor comprising an electronic circuit configured to wirelessly transmit biomedical measurement data.

13. The biomedical sensor according to claim 1, wherein the biomedical sensor is a wireless biomedical sensor comprising an electronic circuit configured to store measurement data into local memory over a predefined period of time.

* * * * *